United States Patent
Lubatschowski

(10) Patent No.: US 10,912,675 B2
(45) Date of Patent: Feb. 9, 2021

(54) GLAUCOMA DRAINAGE IMPLANT

(71) Applicant: ROWIAK GMBH, Hannover (DE)

(72) Inventor: Holger Lubatschowski, Hannover (DE)

(73) Assignee: ROWIAK GmbH, Hannover (DE)

(*) Notice: Subject to any disclaimer, the term of this patent is extended or adjusted under 35 U.S.C. 154(b) by 294 days.

(21) Appl. No.: 15/906,018

(22) Filed: Feb. 27, 2018

(65) Prior Publication Data
US 2018/0250166 A1 Sep. 6, 2018

(30) Foreign Application Priority Data
Mar. 3, 2017 (DE) .......... 10 2017 104 543

(51) Int. Cl.
- *A61F 9/007* (2006.01)
- *A61F 9/00* (2006.01)
- *A61F 9/008* (2006.01)

(52) U.S. Cl.
CPC ........ *A61F 9/00781* (2013.01); *A61F 9/0017* (2013.01); *A61F 2009/00865* (2013.01); *A61F 2009/00891* (2013.01); *A61F 2210/0047* (2013.01); *A61F 2240/001* (2013.01)

(58) Field of Classification Search
CPC ............. A61F 9/00781; A61F 9/0017; A61F 2009/00865; A61F 2009/00891; A61F 2210/0047; A61F 2240/001
See application file for complete search history.

(56) References Cited

U.S. PATENT DOCUMENTS

| | | | |
|---|---|---|---|
| 5,171,213 A * | 12/1992 | Price, Jr. ............. | A61F 9/00781 604/294 |
| 7,641,627 B2 * | 1/2010 | Camras ............... | A61F 9/00781 604/264 |
| 8,758,331 B2 | 6/2014 | Lubatschowski et al. | |
| 9,603,743 B2 | 3/2017 | Rathjen et al. | |
| 2008/0039769 A1 * | 2/2008 | Peyman ................... | A61F 7/02 604/20 |
| 2009/0048586 A1 | 2/2009 | Krueger et al. | |
| 2012/0172852 A1 | 7/2012 | Lubatschowski et al. | |
| 2012/0310225 A1 | 12/2012 | Lubatschowski et al. | |
| 2013/0274725 A1 | 10/2013 | Rathjen et al. | |
| 2015/0257931 A1 * | 9/2015 | Sanchez ............. | A61F 9/00781 604/9 |
| 2016/0058615 A1 | 3/2016 | Camras et al. | |

(Continued)

FOREIGN PATENT DOCUMENTS

| | | |
|---|---|---|
| AU | 20100209664 B2 | 8/2010 |
| AU | 20100209664 A1 | 7/2011 |
| DE | 19916653 | 10/2000 |

(Continued)

*Primary Examiner* — Leslie R Deak
*Assistant Examiner* — Bibhor P Regmi
(74) *Attorney, Agent, or Firm* — Price Heneveld LLP

(57) ABSTRACT

A glaucoma drainage implant comprising a pressure relief valve via which aqueous humor can be drained. The pressure relief valve has a pressure relief flap which is movably connected with a base plate of the implant, which is to be embedded in a sclera, wherein the pressure relief flap has an actuation area by means of which the pressure relief flap can be mobilized non-invasively during a post-operative healing phase or thereafter. The actuation area is preferably designed as a thermomechanically active area.

13 Claims, 3 Drawing Sheets

(56) References Cited

U.S. PATENT DOCUMENTS

2016/0317349 A1   11/2016  Rathjen et al.
2019/0388273 A1*  12/2019  Ferentini ............. A61F 9/00781

FOREIGN PATENT DOCUMENTS

| ES | 2347928 | 11/2010 |
| ES | 2369056 | 11/2011 |
| HK | 1112174 | 7/2013 |

* cited by examiner

GLAUCOMA DRAINAGE IMPLANT

CROSS-REFERENCE TO FOREIGN PRIORITY APPLICATION

The present application claims the benefit under 35 U.S.C. §§ 119(b), 119(e), 120, or 365(c) of DE 02017104543.0 filed Mar. 3, 2017.

FIELD OF THE INVENTION

The present invention relates to a glaucoma drainage implant comprising a pressure relief valve via which the aqueous humor can be drained.

BACKGROUND OF THE INVENTION

Glaucoma is one of the most frequent causes of blindness worldwide. It produces an irreversible degeneration of the retinal ganglion cells. If medication or laser treatment fails to take effect, the underlying increase in intraocular pressure must be lowered by a surgical procedure. The most frequently used method in this regard is trabeculectomy. If the latter fails or is contraindicated, the use of drainage implants is the means of choice.

A general distinction can be made, with regard to current implants, between systems with and systems without a valve. Implants without a valve involve the additional risk of postoperative hypotonia due to the lack of closure following a lowering of pressure. The so-called Ahmed implant is an implant known from the prior art and has a valve which prevents hypotonia. However, long-term outcomes do not show any significant differences compared to trabeculectomy.

The object of the present invention is to provide a glaucoma drainage implant which favors an improved long-term outcome.

This object is achieved by a glaucoma drainage implant comprising a pressure relief valve via which aqueous humor can be drained, the pressure relief valve having a pressure relief flap which is movably connected with a base plate of the implant which is to be embedded in a sclera, the pressure relief flap having an actuation area by means of which the pressure relief flap can be mobilized non-invasively during a post-operative healing phase or thereafter.

The invention includes the realization that fibrovascular encapsulation (caused by formation of collagen) of the implant frequently occurs as a foreign body response to the implant, and is quite a significant complication. After injuries or surgical operations, the human body tries to close the defective wound area. For that reason, inflammation mediators are released at elevated levels in the area where operation injuries have occurred, in order to cause tissue to heal, even with defects in some cases. The formation of inflammation mediators gives rise to fibrosis (formation of collagen fibers) and enhanced formation of protein and inflamematory cells in the aqueous humor (the liquid formed in the eye for regulating intraocular pressure, in addition to providing nutrients). This can lead not only to clogging of a glaucoma drainage implant placed in the eye, but also to growth of a scleral flap created during implant surgery to ensure filtration. This prevents the desired drainage of aqueous humor, thus resulting in a further increase in intraocular pressure.

In contrast to the prior art, the glaucoma drainage implant according to the invention provides the advantage that fibrotic encapsulation can be prevented by the actuation area provided in the pressure relief flap. It is now possible to reduce or indeed to completely avoid any undesired functional restriction of the pressure relief valve by mobilizing it non-invasively. It is also possible, advantageously, to forego the use of cytotoxins, such as mitomycin C or 5-fluoruracil, and thus prevent feared, late-onset sterile endophthalmitis.

In one preferred variant, the actuation area has a thermomechanically active area, which allows the pressure relief flap to be mobilized non-invasively by a change in temperature. The actuation area is preferably provided in the form of a shape-memory material or includes such a material. The shape-memory material advantageously has a two-way memory effect. The shape-memory material may be a shape-memory polymer or a shape-memory alloy or include such a polymer or alloy.

In the context of the present invention, mobilizing the pressure relief flap should be understood as opening the pressure relief flap by inputting heat in the vicinity of the pressure relief flap and as automatic closing of the pressure relief flap on cooling. Automatic closing need not necessarily mean complete closure of the pressure relief flap. Rather, the implant or the pressure relief flap can be designed in such a way that it adopts a slightly open condition on cooling, depending on requirements, in order to allow aqueous humor to drain sufficiently.

In the context of the present invention, with regard to an actuation area designed as a thermomechanically active area, mobilization of the pressure relief flap should be understood as opening the pressure relief flap by inputting an amount of heat into said area effectively, and automatic closure of the pressure relief flap after extraction of the heat from the thermomechanically active area. Alternatively, the pressure relief flap can be opened by an amount of heat which is effectively extracted from the area, and automatic closure of the pressure relief flap can be realized accordingly by re-inputting the heat into that area.

Automatic closing need not necessarily mean complete closure of the pressure relief flap. The implant or the pressure relief flap can be so designed, instead, that it adopts a slightly open condition at human body temperature, depending on requirements, in order to allow aqueous humor to drain sufficiently.

In one preferred variant, the pressure relief flap of the glaucoma drainage implant has an actuation area which is provided in the form of a thermomechanically active area. A shape-memory alloy may be advantageously used for this purpose. This has safety advantages, in particular. The pressure relief flap can thus be activated and opened by inputting heat.

In one preferred variant, the implant is free of any drainage tube.

It has been found to be advantageous when the thermomechanically active area is embodied as a shape-memory alloy. The thermomechanically active area, in particular, a thermomechanical area embodied as a metal plate, can be fully enclosed in the pressure relief flap. The thermoelastic area may include nitinol, for example, or a metal alloy. The thermomechanically active area in the form of a shape-memory material may be advantageously enclosed in the pressure relief flap.

It has been found to be advantageous when the implant is disk-shaped. The implant preferably has a thickness of at most 0.8 mm and/or a width or diameter of at most 6 mm. This allows the implant to be placed near the corneal limbus or Schlemm's canal, and a complex drainage line to be dispensed with.

In another preferred variant, the pressure relief flap is movably connected with the base plate via a flexure joint. This allows a particularly compact and low-maintenance design of the implant. The pressure relief flap and the base plate may be integral with each other.

It has been found to be particularly advantageous when the base plate is step-shaped. Such a step-shaped base plate, in which the steps in the base plate are formed in a radial direction of the eye, helps to prevent sticking of the conjunctiva or Tenon's capsule and the pressure relief flap.

In another preferred variant, the pressure relief flap is framed by the base plate. The base plate is preferably annular in shape, with the pressure relief flap being circular in shape. Alternatively, the base plate may be designed in the shape of a frame. In this case, the pressure relief flap has an outer shape that is rectangular or square.

It has been found to be advantageous when the pressure relief flap includes silicone, and it is particularly preferred if the pressure relief flap, apart from the thermomechanically active area, consists of silicone. The entire glaucoma drainage implant, apart from the thermomechanically active area, may thus consist of silicone.

It has been found to be advantageous when the pressure relief flap has surface structuring on the side facing the cornea. In principle, however, the surface structuring may also be provided on the side facing away from the cornea, or on both sides.

In one particularly preferred variant, the pressure relief valve is designed not to drain aqueous humor until the intraocular pressure exceeds 15 mmHg (about 20 mBar). In other words, the pressure relief valve is designed to regulate the intraocular pressure.

The object of the invention is likewise achieved by a method of implanting a glaucoma drainage implant into a human or animal eye, the method comprising the steps of creating a scleral bed in a sclera of the eye, said scleral bed having a drainage channel; implanting a glaucoma drainage implant as described in the foregoing into the scleral bed in such a way that the base plate closes the scleral bed water-tightly; and mobilizing the pressure relief flap, during or after a post-operative healing phase for the implant, by means of an energy source which generates a temperature gradient.

The method can be designed appropriately and advantageously by incorporating the features of the glaucoma drainage implant described above.

For example, the pressure relief flap of the glaucoma drainage implant used in the method may have an actuation area in the form of a thermomechanically active area.

In one preferred variant of the method, heat is supplied (to produce a temperature increase in the thermomechanically active area) by irradiating with light, preferably infrared light, which is not absorbed by the surrounding tissue or only to a minor extent. Absorption of radiation by the material of the implant or part of the implant results in the increase in temperature. The thermal effect may be concentrated locally in a desired manner, by providing coloring which strongly absorbs the wavelengths being used, in the regions of the implant which are to heat up.

Alternatively, or additionally thereto, a temperature increase can also be achieved inductively or by applying an electric current. In this case, the shape-memory material is designed to be electrically conductive, such that an eddy current which causes heating can be induced in the material by exposing it to an externally applied, high-frequency magnetic field. A pole shoe may be deployed and appropriately disposed in order to concentrate the field lines.

Further advantages can be seen from the following description of the Figures. The Figures show various embodiments of the present invention. The Figures, the description and the claims contain numerous features in combination. A skilled person will expediently view the features singularly as well and will combine them to form other useful combinations.

DETAILED DESCRIPTION OF THE EMBODIMENTS

In the Figures, the same or corresponding elements or units are each provided with the same and/or the corresponding reference signs. When an element or a unit has already been described with reference to a particular Figure, a detailed description is dispensed with when discussing another Figure. However, it is to be understood that the present disclosure may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale.

A preferred variant of the glaucoma drainage implant according to the invention shall now be described with reference to FIGS. 1A and 1B.

Figure 1A:
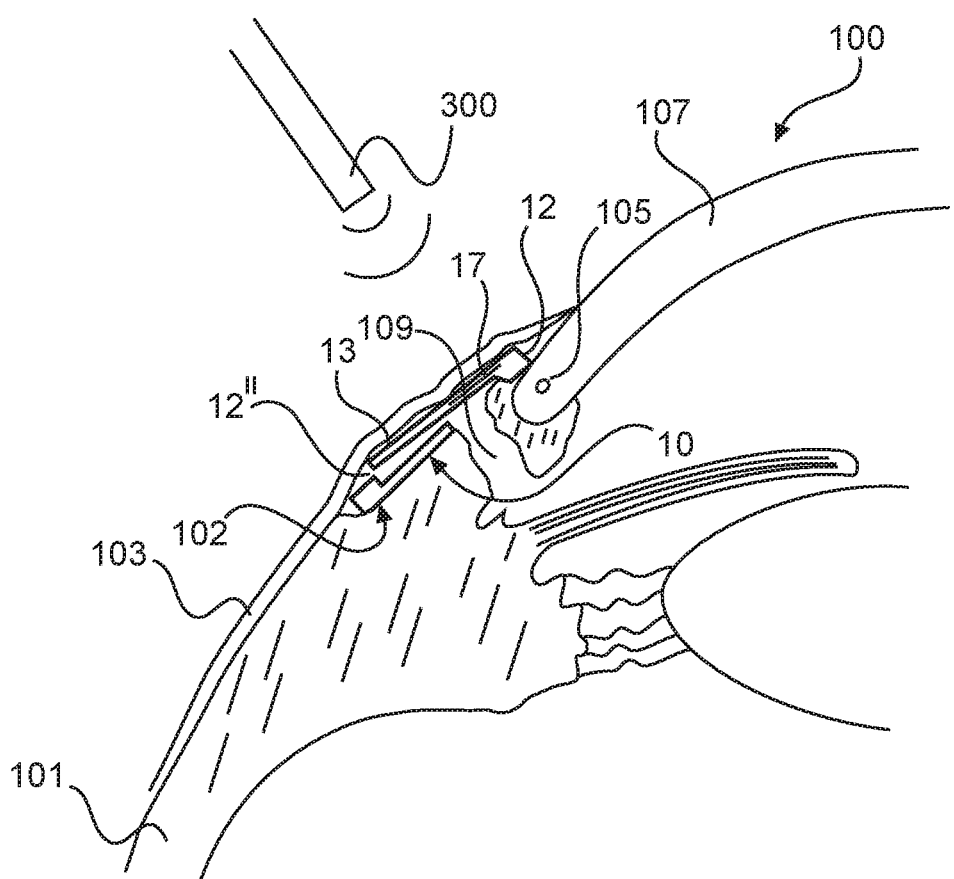
FIG. 1A is a cross-sectional side view of a first preferred embodiment of the glaucoma drainage implant according to the invention, in the implanted position inside an eye.

FIG. 1A shows a human eye 100 in a cross section close to the corneal limbus. The cornea 107, in the lower part of which Schlemm's canal 105 is drawn, can be seen in the upper part of FIG. 1A.

A scleral bed 102 with a drainage channel 109 is formed in the sclera 101. The scleral bed 102 may be produced by means of a laser, for example, or may also be prepared manually.

A glaucoma drainage implant 10 is embedded in scleral bed 102. Implant 10 functions as a pressure relief valve via which the aqueous humor can be drained. Implant 10 functioning as a pressure relief valve has a pressure relief flap 13, which is movably connected with a base plate 12 of implant 10, which is embedded in the sclera 101.

As can be seen from FIG. 1A, base plate 12 is fitted into scleral bed 102 in such a way that the latter is laterally sealed against the sclera 101, so that, apart from the path via drainage channel 109 and pressure relief flap 13, no aqueous humor can drain off.

Drainage channel 109 is formed at the bottom of scleral bed 102. In the embodiment shown in a FIG. 1A, implant 10 is disk-shaped and is shown here in cross section. The implant has a thickness of at most 0.8 mm (in the radial direction R in respect of eye 100) and a width of at most 6 mm (in relation to tangential direction T).

Annular base plate 12 laterally surrounds pressure relief flap 13. Pressure relief flap 13 is movably connected with base plate 12 via an attachment area 12'. The attachment area serves as a flexure joint. The opening region 12" of pressure relief flap 13 is located on the opposite side.

As can likewise be seen from FIG. 1A, base plate 12 is step-shaped, in relation to the radial direction R, base plate 12 having a greater thickness in attachment area 12' than in the opening region 12" opposite attachment area 12'.

In the condition shown in FIG. 1A, pressure relief flap 13 is slightly open, so it is possible for an amount of aqueous humor to drain through drainage channel 109 and the implant functioning as a valve.

As can also be seen from FIG. 1A, pressure relief flap 13 projects, at least in a portion thereof, over and beyond drainage channel 109, so it is possible to close the drainage channel by means of pressure relief flap 13, or to open it again in the event of excessive pressure. The implant functioning as a pressure relief valve is designed not to drain aqueous humor until the intraocular pressure exceeds 20 mBar.

Figure 1B:
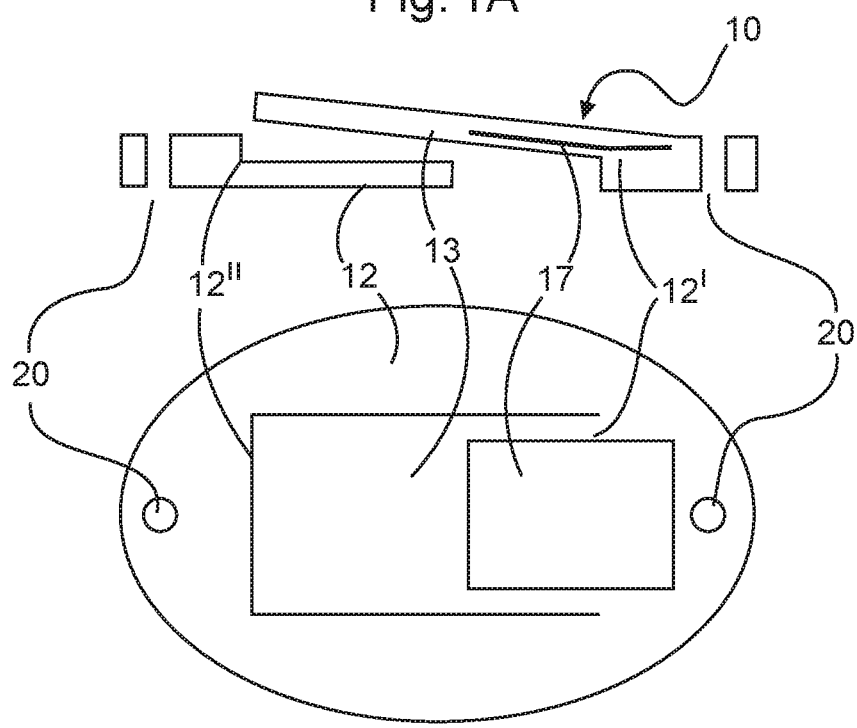
FIG. 1B is a schematic side and top view of a preferred embodiment of the glaucoma drainage implant according to the invention.

As can be seen from FIG. 1B, pressure relief flap 13 has a thermomechanically active area 17, such that pressure relief flap 13 can be mobilized non-invasively by means of heat (produced by laser irradiation or inductively) in a post-operative healing phase.

In the embodiment shown here, thermomechanical area 17 is provided in the form of a metal plate which consists of a shape-memory alloy and which is enclosed inside pressure relief flap 13 and attachment area 12'. Pressure relief flap 13 and attachment area 12' consist, apart from the thermomechanical areas, of silicone.

The implant can be affixed to the sclera by a thread using eyelets 20 attached to the implant.

If infrared laser radiation 300, for example, is beamed in the direction of the thermomechanical area 17, a torque acts upon pressure relief flap 13 such that the latter is moved in the radial direction, which is upward in FIG. 1A, and in such a manner is mobilized and opened.

When the thermomechanical part of the valve cools down to body temperature, pressure relief flap 13 closes automatically due to shape recovery of the attachment area 12' which serves as a flexure joint and via which pressure relief flap 13 is connected with base plate 12. If the intraocular pressure is less than 20 mBar, pressure relief flap 13 closes completely.

Figure 2A:
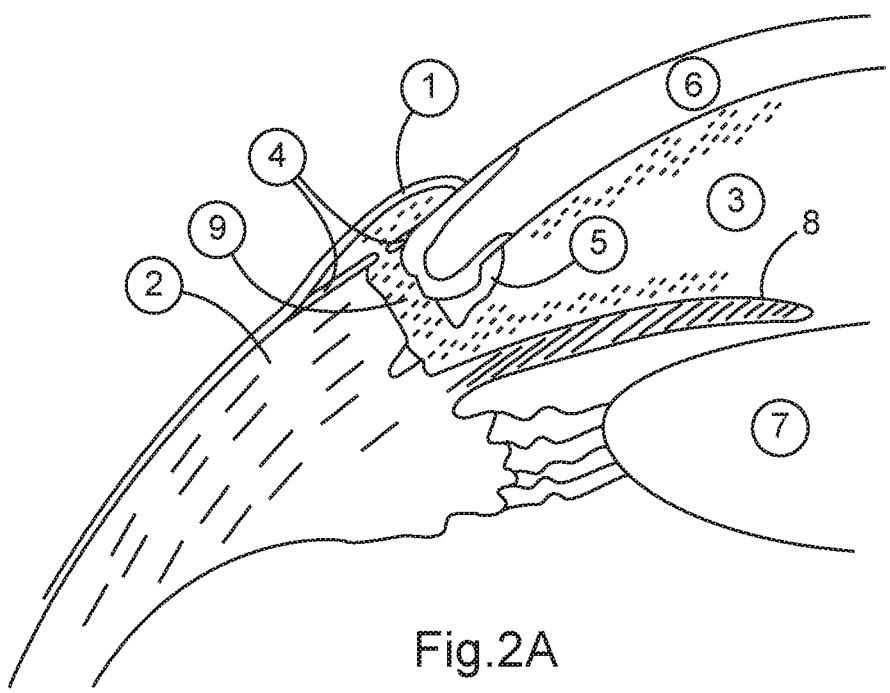
FIGS. 2A, 2B, and 2C are cross-sectional side views of a prior art glaucoma drainage implant, in a normal position following implantation with an adverse outcome.
Figure 2B:
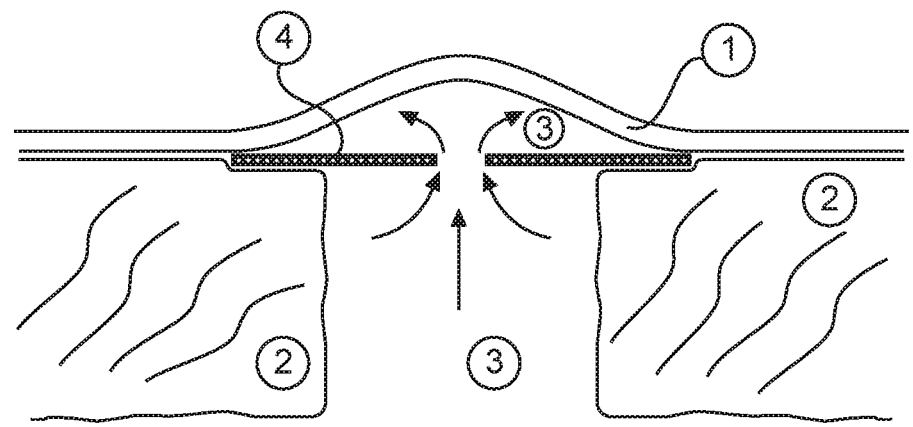
Figure 2C:
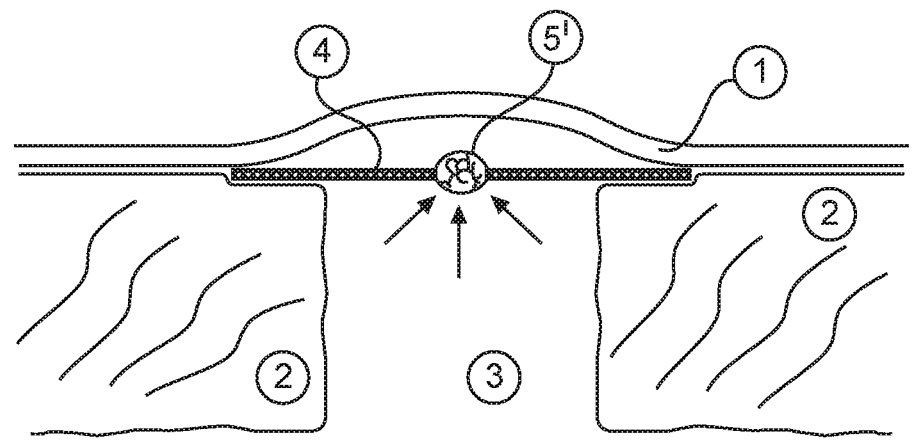

FIGS. 2A, 2B, and 2C show a prior art glaucoma drainage implant in a normal position following implantation with an adverse outcome.

FIG. 2A shows the normal position of an implant 4 in the eye for draining aqueous humor 3. The sclera 2 and the trabecular meshwork 5 have been surgically perforated 9. The aqueous humor 3 flowing out of the anterior chamber through an implant opening is held back by the conjunctiva 1, under which a bleb usually forms. The Figure also shows the cornea 6 of the eye, the iris 8 and the lens 7.

In FIG. 2B, the condition immediately after implantation of the implant is shown. The implant 4 is located between the conjunctiva 1 and the sclera 2. The sclera is interrupted by an aperture which is surgically cut and where the aqueous humor 3 flows through an opening in the implant to the outside under the conjunctiva, where it forms a bleb.

FIG. 2C shows the condition after implantation. The opening of the implant is clogged by fibrotic deposits 5'. Aqueous humor 3 can no longer drain freely.

Figure 3A:
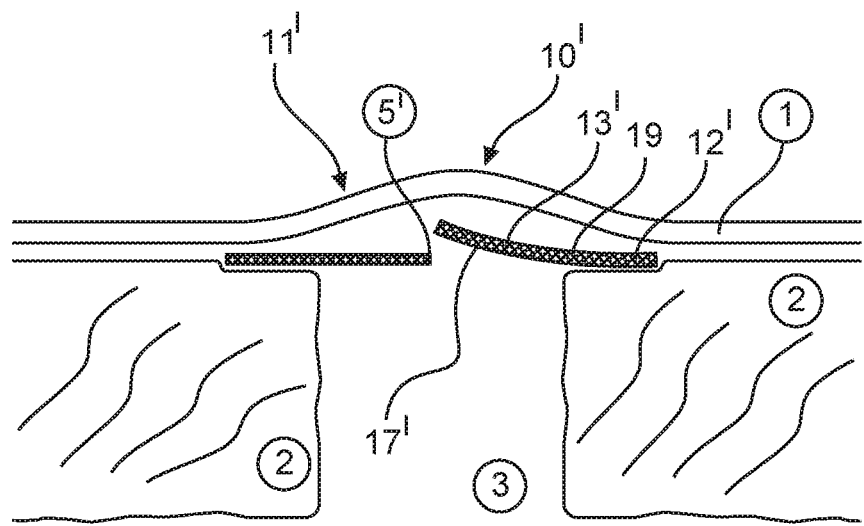
FIGS. 3A and 3B are a second preferred embodiment of the glaucoma drainage implant according to the invention, following implantation with an advantageous outcome.
Figure 3B:
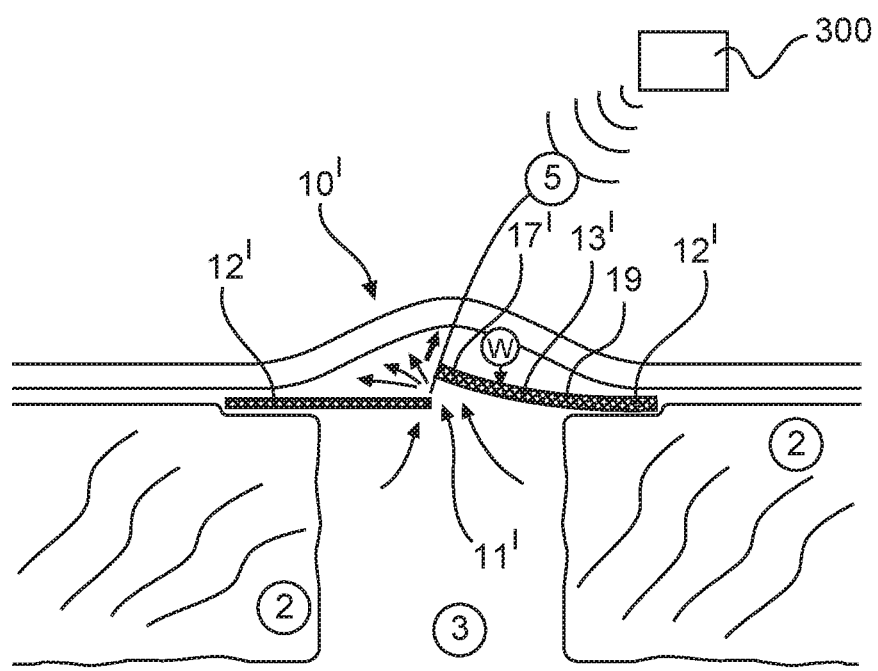

FIGS. 3A and 3B show a second preferred embodiment of the glaucoma drainage implant 10' according to the invention, following implantation with an advantageous outcome.

As can be seen from FIG. 3A, the glaucoma drainage implant 10' functions as a pressure relief valve 11' via which the aqueous humor 3 can be drained. Pressure relief valve 11' has a pressure relief flap 13' which is movably connected with a base plate 12' of implant 10', which is to be embedded in sclera 2. Pressure relief flap 13 has an actuation area in the form of a thermomechanically active area comprising a shape-memory material 17' with a two-way memory effect, by means of which the pressure relief flap 13' can be non-invasively mobilized during a post-operative healing phase or thereafter. Pressure relief flap 13 is movably connected with base plate 12 via an attachment area 12' which serves as a flexure joint.

In FIG. 3A, an opening in implant 10', to be released by pressure relief flap 13', is clogged by fibrotic deposits 5'.

FIG. 3A shows the condition after the movable pressure relief flap 13' has been moved one or more times. The movement has ensured that the fibrotic deposits are broken up and that the path of the aqueous humor 3 to the outside (in the direction shown by the arrows) has been cleared.

Pressure relief flap 13' is mobilized by means of an infrared source 300 with which an amount of heat W is transferred to the thermomechanically active area comprising the shape-memory material 17'.

It will be understood that any described processes or steps within described processes may be combined with other disclosed processes or steps to form structures within the scope of the present disclosure. The exemplary structures and processes disclosed herein are for illustrative purposes and are not to be construed as limiting.

It will be understood by one having ordinary skill in the art that construction of the present disclosure and other components is not limited to any specific material. Other exemplary embodiments of the disclosure disclosed herein may be formed from a wide variety of materials, unless described otherwise herein.

It is also important to note that the construction and arrangement of the elements of the present disclosure as shown in the exemplary embodiments is illustrative only. Although only a few embodiments of the present innovations have been described in detail in this disclosure, those skilled in the art who review this disclosure will readily appreciate that, unless otherwise described, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating positions, and arrangement of the desired and other exemplary embodiments without departing from the spirit of the present innovations.

It is also to be understood that variations and modifications can be made on the aforementioned structures and methods without departing from the concepts of the present invention, and further it is to be understood that such concepts are intended to be covered by the following claims unless these claims by their language expressly state otherwise.

LIST OF REFERENCE SIGNS

3 Aqueous humor
5 Trabecular meshwork
5' Fibrotic deposits
6, 107 Cornea
7 Lens
8 Iris
10, 10' Glaucoma drainage implant
11, 11' Part of the implant acting as pressure relief valve
12 Base plate
12' Attachment area
12" Opening region
13, 13' Pressure relief flap
17 Shape memory material
20 Eyelet
100 Eye
2, 101 Sclera
102 Scleral bed
1, 103 Conjunctiva
105 Schlemm's canal
9, 109 Surgical perforation, drainage channel
300 Infrared source
W Heat

The invention claimed is:

1. A glaucoma drainage implant comprising a pressure relief valve via which aqueous humor can be drained, wherein the pressure relief valve has a pressure relief flap which is movably connected with a base plate of the implant, which is to be embedded in a sclera, wherein the pressure relief flap has an actuation area by means of which the pressure relief flap can be mobilized non-invasively during a post-operative healing phase or thereafter, and wherein the actuation area has a thermomechanically active area comprising a shape-memory material with a two-way memory effect, such that the pressure relief flap can be mobilized non-invasively by a change in electromagnetic radiation.

2. The implant of claim 1, wherein the electromagnetic radiation is heat.

3. A glaucoma drainage implant comprising a pressure relief valve via which aqueous humor can be drained, wherein the pressure relief valve has a pressure relief flap which is movably connected with a base plate of the implant, which is to be embedded in a sclera, wherein the pressure relief flap has an actuation area by means of which the pressure relief flap can be mobilized non-invasively during a post-operative healing phase or thereafter, and wherein the actuation area has a thermomechanically active area comprising a shape-memory material with a two-way memory effect, such that the pressure relief flap can be mobilized non-invasively by a change in temperature.

4. The implant of claim 1, wherein the electromagnetic radiation is light.

5. The implant of claim 1, wherein the electromagnetic radiation is infrared radiation.

6. A glaucoma drainage implant comprising a pressure relief valve via which aqueous humor can be drained, wherein the pressure relief valve has a pressure relief flap which is movably connected with a base plate of the implant, which is to be embedded in a sclera, wherein the pressure relief flap has an actuation area by means of which the pressure relief flap can be mobilized non-invasively during a post-operative healing phase or thereafter, and wherein the actuation area has a thermomechanically active area comprising a shape-memory material with a two-way memory effect, such that the pressure relief flap can be mobilized non-invasively by a change in induction heating.

7. A glaucoma drainage implant comprising a pressure relief valve via which aqueous humor can be drained, wherein the pressure relief valve has a pressure relief flap which is movably connected with a base plate of the implant, which is to be embedded in a sclera wherein the pressure relief flap has an actuation area b means of which the pressure relief flap can be mobilized non-invasively during a post-operative healing phase or thereafter, wherein the pressure relief flap is movably connected with the base plate via an attachment area which serves as a flexure joint.

8. A glaucoma drainage implant comprising a pressure relief valve via which aqueous humor can be drained, wherein the pressure relief valve has a pressure relief flap which is movably connected with a base plate of the implant, which is to be embedded in a sclera, wherein the pressure relief flap has an actuation area by means of which the pressure relief flap can be mobilized non-invasively during a post-operative healing phase or thereafter, and wherein the base plate is step-shaped, the base plate having a greater thickness in an attachment area of the pressure relief flap than in an opening region of the pressure relief flap opposite the attachment area.

9. The implant of claim 1, wherein the pressure relief flap is framed by the base plate.

10. The implant of claim 1, wherein the pressure relief flap includes silicone.

11. The implant of claim 1, wherein the pressure relief flap has surface structuring on the side facing a cornea.

12. The implant of claim 1, wherein in the pressure relief valve is designed not to drain aqueous humor until the intraocular pressure exceeds 20 mBar (15 mmHg).

13. A method of implanting a glaucoma drainage implant into a human or animal eye, the method comprising the steps of:
creating a scleral bed in a sclera of the eye, said scleral bed having a drainage channel;
implanting a glaucoma drainage implant into the scleral bed in such a way that the base plate closes the scleral bed water-tightly, the glaucoma drainage implant comprising a pressure relief valve via which aqueous humor can be drained, wherein the pressure relief valve has a pressure relief flap which is movably connected with a base plate of the implant, which is to be embedded in a sclera, and wherein the pressure relief flap has an actuation area by means of which the pressure relief flap can be mobilized non-invasively during a post-operative healing phase or thereafter; and
non-invasively mobilizing the pressure relief flap, during or after a post-operative healing phase for the implant;

wherein the step of non-invasively mobilizing is by means of an energy source which generates a temperature gradient.

* * * * *